United States Patent [19]
Mori et al.

[11] Patent Number: 4,904,257
[45] Date of Patent: Feb. 27, 1990

[54] FIBROUS BONE FILLER AND PROCESS OF PRODUCING THE SAME

[75] Inventors: Shoichi Mori, Ooimachi; Shigeo Fujii, Kawagoe; Masao Yoshizawa, Tokyo; Kenji Miyasaka, Ooimachi; Jyoichi Tabuchi, Ooimachi; Kazufumi Egawa, Ooimachi; Minoru Hirano, Kurume; Yoshikazu Yoshida, Fukuoka, all of Japan

[73] Assignees: Toa Nenryo Kogyo K. K.; Asahi Kogaku Kogyo Kabushiki Kaisha, both of Tokyo, Japan

[21] Appl. No.: 215,782

[22] Filed: Jul. 6, 1988

Related U.S. Application Data

[62] Division of Ser. No. 28,589, Mar. 20, 1987, abandoned.

[30] Foreign Application Priority Data

Mar. 20, 1986 [JP] Japan ................................. 61-63044

[51] Int. Cl.$^4$ .............................................. A61F 1/00
[52] U.S. Cl. ..................................... 623/16; 106/161; 106/209; 106/35; 264/220; 428/221
[58] Field of Search .......................... 623/16, 66, 901; 514/54

[56] References Cited
U.S. PATENT DOCUMENTS

| 4,097,935 | 7/1978 | Jarcho | 106/35 |
| 4,172,128 | 10/1979 | Thiele et al. | 623/16 |
| 4,330,514 | 5/1982 | Nagai et al. | 106/35 |
| 4,603,050 | 7/1986 | Veerme et al. | 514/200 |
| 4,613,577 | 9/1986 | Tagai et al. | 501/35 |
| 4,655,777 | 4/1987 | Dunn et al. | 623/16 |
| 4,659,617 | 4/1987 | Fujii et al. | 428/211 |
| 4,776,890 | 10/1988 | Chu | 106/35 |

FOREIGN PATENT DOCUMENTS

| 104640 | 4/1984 | European Pat. Off. | 623/16 |
| 0146398 | 12/1984 | European Pat. Off. | |
| 0174827 | 9/1985 | European Pat. Off. | |

Primary Examiner—Theodore Morris
Attorney, Agent, or Firm—Birch, Stewart, Kolasch & Birch

[57] ABSTRACT

A fibrous bone filler having an excellent biocompatibility. The bone filler comprises fibers containing hydroxyl apatite. The hydroxyl apatite is "intact", that is, the hydroxyl apatite substantially retains its hydroxyl groups.

20 Claims, 1 Drawing Sheet

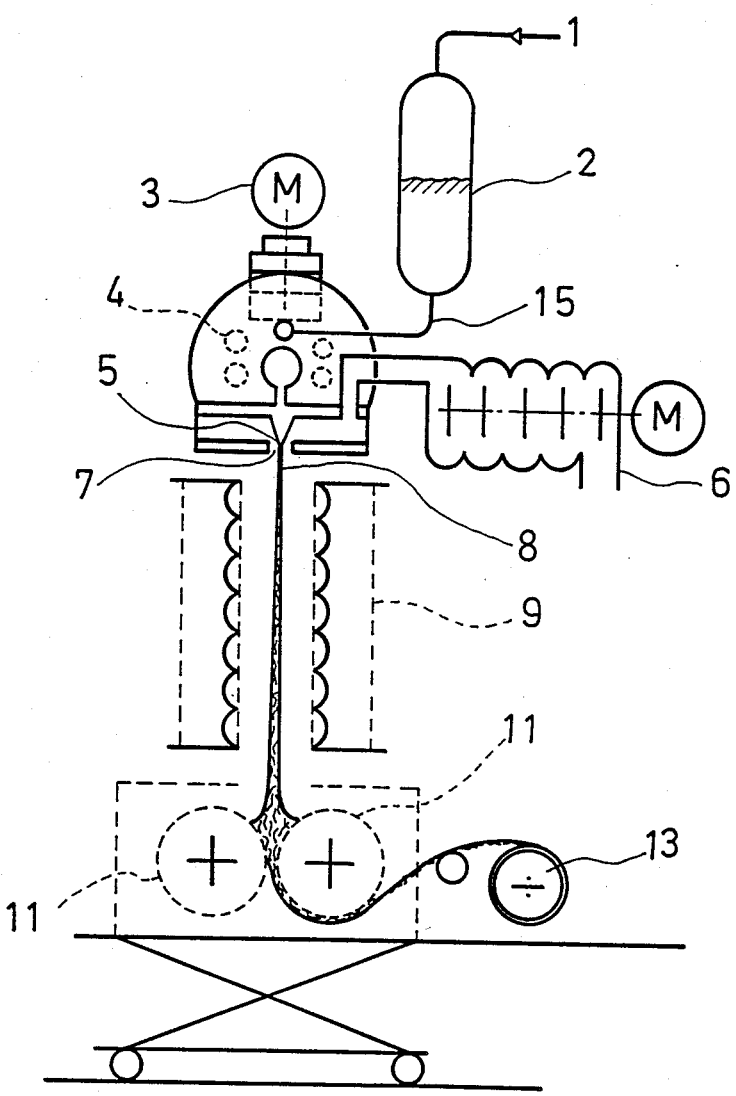

FIBROUS BONE FILLER AND PROCESS OF PRODUCING THE SAME

This application is a divisional of application Ser. No. 028,589 filed on Mar. 20, 1987, now abandoned.

BACKGROUND OF THE INVENTION

I. Field of the Invention

This invention relates to a bone filler which is filled in a defect or a void of a bone.

II. Description of the Prior Art

A defect or a void may be formed in a bone due to, for example, a fracture or an operation for eliminating a bone tumor. Conventionally, to fill such a defect or void in the bone, autoplasty is conducted by filling with a bone material collected from another portion of the patient. In other cases, the bone material is collected from a near relative of the patient. However, in those methods, the bone material to be filled in the defect or void must be collected by conducting an operation from the patient or the near relative of the patient. Thus, the burden on the patient or the near relative of the patient is great. Further, when the defect or the void to be filled is large, it may be difficult to obtain sufficient bone material.

To overcome this problem, artificial bone fillers have been developed. The materials of the known bone fillers include metals and ceramics. Among these, from the view point of biocompatibility, calcium phosphate-based compounds are preferred. Among the calcium phosphate-based compounds, it is known that hydroxyl apatite which is a component of the bone is especially preferred. Conventional hydroxyl apatite bone fillers include those in the forms of granules, powder (Japanese Patent Disclosure (Kokai) No. 54841/81) or fibers (Japanese Patent Disclosure (Kokai) No. 7-117621). The bone filler in the form of granules or powder has the drawback that it is inconvenient to handle in an operation. As to the bone filler in the form of fibers, although the handling is easier than those in the form of granules or powder, the hydroxyl groups of the hydroxyl apatite are decomposed when the fibers are melt-spun, so that the biocompatibility is reduced.

SUMMARY OF THE INVENTION

Accordingly, an object of the present invention is to provide a bone filler which has an excellent biocompatiblity, which is easy to handle, and which fits into the complicated shape of the defect or the void in the bone.

This and other objects of the present invention may be accomplished by providing a fibrous bone filler comprising fibers containing intact hydroxyl apatite. The term "intact" herein used means that the hydroxyl apatite substantially retains its hydroxyl groups. The filler of the present invention is preferably in the form of a non-woven fabric, cotton, absorbent cotton, or roving.

Since the bone filler of the present invention comprises the "intact" hydroxyl apatite, the biocompatibility of the bone filler is very high, so that rejection reaction does not occur, and giant cells do not emerge. Further, since the bone filler is fibrous, it may be pushed into the defect or the void of a complicated shape. Thus, the handling thereof in an operation is easy and it fits well into the defect or the void. Further, the bone filler has a great osteogenesis-causing ability, so that the defect or the void may be recovered in a shorter time than in the conventional methods. Still further, since the bone filler of the present invention has the intact hydroxyl apatite, it is well taken by the bone when a new bone tissue generates, and it becomes a part of the bone.

BRIEF DESCRIPTION OF THE DRAWING

The accompanying drawing shows an schematic view for explaining a process of producing the bone filler of the present invention.

DETAILED DESCRIPTION OF THE PREFERRED EMBODIMENTS

As described above, if the hydroxyl apatite is melt-spun into a fiber, at least a part of the hydroxyl groups of the hydroxyl apatite is decomposed, so that the biocompatibility of the bone filler is reduced. The present inventors have found a process by which a fiber containing intact hydroxyl apatite which retains substantially all of the hydroxyl groups may be obtained. The intact hydroxyl apatite fiber may be obtained by a solution spinning method which employs a specific binder. The method will be described later in detail.

The fibers constituting the fibrous bone filler of the present invention comprise intact hydroxyl apatite. The content of the hydroxyl apatite is preferably at least 25% by weight, and more preferably at least 50% by weight. Since hydroxyl apatite is a component of the bone, from the view point of biocompatibility, it is preferred that the fiber essentially consist of intact hydroxyl apatite. It should be noted, however, if the fiber essentially consists of hydroxyl apatite, the strength thereof is reduced. Thus, for increasing the strength of the fiber, a reinforcing material, such as, for example, calcium phosphate-based compound and water glass, may be incorporated in the fiber Among the reinforcing materials, from the view point of biocompatibility, calcium phosphate-based compounds are preferred. The content of the reinforcing material in the fiber is usually 25% by weight or less. The filler may contain water. The water content in the filler is usually 50% by weight or less.

The diameter of the fiber constituting the bone filler of the present invention is not limited, but typically from 1 to 30 $\mu$m, and preferably 1 to 10 $\mu$m. The weight of the fibrous bone filler of the present invention is also not limited, but usually 5 g/m$^2$ to 500 g/m$^2$.

The fibrous bone filler of the present invention may be produced by a solution spinning process which utilizes a specific binder. The binder should be harmless to the human body and is preferred to be water-soluble. The macromolecules which satisfy these conditions may preferably be used. Among the water-soluble macromolecules which may be used as the binder, preferred are polyvinyl alcohol, polycarboxymethyl cellulose, hydroxypropyl cellulose, collagen, pullulan and chitin. Among these, pullulan is most preferred. The molecular weight of the macromolecules may preferably be 20,000 to 2,000,000, and more preferably 50,000 to 1,000,000. These macromolecules may be used independently or in combination.

The hydroxyl apatite which is used as a starting material of the process may preferably be in the form of super fine particles. The super fine particles are preferably in the form of a rod, of which diameter is preferably 5 nm to 1 $\mu$m. Such hydroxyl apatite particles may be produced by a well-known conventional method. For example, they can be produced by adding an aqueous phosphoric acid solution to a basic solution (pH7–11) containing calcium ions.

In the process of producing the fibrous bone filler of the present invention, an aqueous suspension containing the above-described binder and hydroxyl apatite is used as the starting material. The aqueous suspension preferably contains 10–90% by weight, more preferably 50–70% by weight, and still more preferably 60–65% by weight of water; 5–70% by weight, more preferably 15–30% by weight, and still more preferably 15–20% by weight of hydroxyl apatite; and 5–40% by weight, more preferably 15–30% by weight, and still more preferably 20–25% by weight of the binder. If the hydroxyl apatite content is less than 5% by weight, the strength of the produced fibrous material is small, and if the hydroxyl apatite content is more than 70% by weight, the viscosity of the aqueous suspension becomes undesirably too high.

To increase the fluidity of the suspension to improve the dispersion of the hydroxyl apatite, a surface active agent of carbonic acid-based, plasticizer and/or softening agent may be added to the suspension, if desired. A defoaming agent may also be added. The content of such agents may typically be 0.01–5% by weight. When the above-described reinforcing material is used, the reinforcing material is dispersed in the suspension. It should be noted, however, when the reinforcing material is $Ca_3(PO_4)_2$, it can be formed in the sintering step as described later.

The aqueous suspension may be prepared under a temperature of about 20°–70° C.

An example of the process of producing the fibrous bone filler of the present invention, which utilizes the above-described aqueous suspension as the starting material will now be described referring to the accompanying drawing.

The aqueous suspension is supplied to a tank 2 through a supplying duct 1. The suspension is then supplied to a spinning nozzle 5, and is jetted from the nozzle by gear pumps 4 actuated by a motor 3. Air is supplied from a blower 6 to an air nozzle 7 which encircles the spinning nozzle 5, and is jetted from the air nozzle 7. The velocity of the air flow may be about 5 to about 1000 m/s, and the temperature of the air may be about 20° to 60° C. A plularity of the spinning and air nozzle assemblies may be provided, and the air nozzles may be disposed in a row, or in a circle. By the simultaneous jetting of the aqueous suspension and the air, the aqueous suspension is spun into a bundle of fine fibers 8. The diameter of the fibers may be adjusted by controlling the air velocity, to typically about 1 to 30 μm, and preferably about 1 to 10 μm. The higher the velocity of the air, the smaller the diameter of the fibers. When the air velocity is 1000 m/s, fibers of about 1 μm diameter are obtained. When the air velocity is 300 m/s and 30 m/s, fibers of about 3–5 μm diameter, and 20 μm diameter are obtained, respectively.

The thus formed bundle of fine fibers 8 is then heat-dried by a heater 9. The heater 9 may be, for example, an infrared heater, far infrared heater, or a microwave heater. The fibers are dried and solidified by the heater 9 to the water content of, for example, 10% by weight or less and preferably 7% by weight or less. If the drying is not sufficient, a fibrous material consisting of the fine fibers may not be obtained. The heating temperature varies depending on the amount of the material ejected from the spinning nozzle 5, on the temperature of the air jet, and on the amount of the air jet. Usually, the temperature of the heater 9 is in the range of about 200° to 500° C. (the temperature of the fibers being about 80° to 150° C.) If the heating temperature is too high, the binder may be decomposed.

The thus dried fibers are then collected on a moving collecting means 11 by dropping the fibers on the moving collecting means in an intercrossing manner to obtain a fibrous material. The collecting means 11 may be, for example, a wire net drum or a wire net belt. Two wire net drums rotating in the opposite direction may preferably be used. If the fibers are dropped on the contact portion of the two drums, a voluminous fibrous material in which the intercrossed fibers are three-dimensionally disposed, i.e., a fibrous material in the form of cotton or absorbent cotton, may be obtained. If the fibers are dropped on a portion other than the contact portion of the drums, a planar fibrous material in which the intercrossed fibers are arranged two-dimensionally, i.e., a fibrous material in the form of a non-woven fabric, may be obtained. The fibrous material in the form of a roving may be obtained by using a plularity of spinning nozzles disposed in a circle. By controlling the moving speed of the collecting means, fibrous material of 5 g/m² to 500 g/m² may be obtained. The thus formed fibrous material may be spooled on a reel 13.

It is preferred that the thus obtained fibrous material in which the fibers are bound each other by the binder be sintered to eliminate the binder. The sintering may be conducted under a temperature of about 500° to 1300° C., preferably about 600° to 1200° C., and more preferably about 650° to 1100° C. If the sintering is conducted under a temperature higher than 1300° C., the hydroxyl groups of the hydroxyl apatite may be decomposed. If the sintering is conducted under a temperature of 1100° C. to 1300° C., $Ca_3(PO_4)_2$ is generated, so that the strength of the fibers may be improved.

The thus obtained fibrous bone filler may be filled in a defect or void in a bone. Good results may also be obtained if the fibrous bone filler is used in combination with a hydroxyl apatite filler in the form of granules or powder. The biocompatibility of the bone filler may be further promoted by immersing the filler in water, physiological saline, chondroitin solution, hyaluronic acid solution, or in a collagen solution. The amount of the impregnated liquid is typically about 1 to 20% by weight, preferably 5 to 10% by weight. The preferred solvent of the chondroitin solution and hyaluronic acid solution and collagen solution is water, and the preferred concentration of the solutes is about 1 to 20% by weight. If desired, the thickness of the fibrous bone filler may be controlled by subjecting the bone filler to a calender process. The biocompatibility may also be promoted by using such calendered fibrous material immersed in water, physiological saline, chondroitin solution, hyaluronic acid solution or in a collagen solution.

EXAMPLE 1

An aqueous suspension containing 9% by weight of pullulan powder of which average molecular weight is 200,000, 42% by weight of hydroxyl apatite powder (particles of 5 to 80 nm diameter), 1% by weight of dispersant (carbonic acid-based surface active agent), and 48% by weight of water was vigorously stirred under the room temperature to uniformly disperse the pullulan in the aqueous system. The aqueous suspension was then defoamed. The aqueous suspension was then jetted from a spinning nozzle of 0.3 mm diameter. Air was jetted simultaneously from an air nozzle encircling the spinning nozzle at a velocity of 300 m/s to form a bundle of fibers. The fibers were then heated by an infrared heater to evaporate the water. The dried fibers were dropped on the contact portion of rotating wire net drums rotating in opposite directions with respect to each other, to obtain a fibrous material in the form of cotton. The thus obtained cotton-like hydroxyl apatite fibrous material was sintered at an elevating temperature of 50° C./h up to 1100° C., and was kept at this temperature for 2 hours.

The thus obtained fibrous material in the form of cotton had a weight of about 200 g/m² and had sufficient strength. The average diameter of the fibers constituting the cotton was 5 μm.

In the center portion of the tibiae of twelve cats (male and female), two holes are formed along the longitudinal direction of the bone, to form artificial bone defects. The fibrous bone filler obtained as above was filled in the holes up to the bone marrow cavity.

After 1 week, 2 weeks and 4 weeks from the filling operation of the bone filler, the bone tissues around the holes were separated and were immediately fixed with 10% formalin solution. After removing ash, they were embedded in a resin, and cross sections were prepared. The cross sections were stained by various staining method to prepare pathologic specimens. The specimens were observed with a microscope. The results of the observation were as follows:

After 1 Week

In the portion of the sponge layer contacting the hydroxyl apatite filler, fibroblasts were grown, and new bone beam and osteoblasts were generated. The binding of the hydroxyl apatite with the bone cortex was sparse. Only a portion of the periosteum invaded into the hydroxyl apatite. No foreign body membrane was observed around the hydroxyl apatite.

After 2 Weeks

Generation of new bone beam in the sponge layer, osteogenesis and growth of osteoblasts at the cut edge of the bone cortex were very great. Hydroxyl apatite was tighter than the week 1 group. Periosteum covered substantially the whole hydroxyl apatite. The cortex and the hydroxyl apatite were strongly bound each other by collagen fibers. Generation of giant cells and other foreign body reactions were not observed at all.

After 4 Weeks

The hydroxyl apatite had been constracted, and the intervals between fibers had been made small. The osteogenesis in the sponge layer was further promoted. Osteogenesis at the cortex cut edge was also further promoted. Collagen fibers invaded the hydroxyl apatite. Periosteum completely covered the hydroxyl apatite.

As described above, by using the bone filler of the present invention, the growth of fibroblasts, and generation of bone beam and osteoblasts are observed after only 1 week from the embedment of the hydroxyl apatite filler. If a conventional filler is used, such phenomena are observed after 1 to 3 months from the embedment of the filler. Further, no foreign body reactions occur. As the time elapses, the osteogenesis and growth of osteoblasts are rapidly promoted, so as to cover the whole hydroxyl apatite. Further, newly generated bone tissue is rapidly integrated with the bone tissue at the peripheral portion of the artificial defect. Thus, the bone filler of the present invention has a much greater biocompatibility than the conventional hydroxyl apatite bone fillers, and has an osteogenesis-causing ability.

EXAMPLE 2

The hydroxyl apatite filler in the form of cotton obtained in Example 1 was mixed with hydroxyl apatite powder (spherical hydroxyl apatite particles of 20 to 100 μm diameter which was sintered at 700° C.) in a weight ratio of 5:1, and the test was conducted as in Example 1. Good results as in Example 1 were obtained.

EXAMPLE 3

A fibrous hydroxyl apatite in the form of cotton, of which fibers had an average diameter of 10 μm was obtained by the same manner as in Example 1. The obtained bone filler was tested as in Example 1, and good results as in Example 1 were obtained.

EXAMPLE 4

To the hydroxyl apatite filler obtained in Example 1, water or physiological saline was added, and the wetted hydroxyl apatite filler was tested as in Example 1. Good results as in Example 1 were obtained.

EXAMPLE 5

To the bone filler of Examples 1, 2 and 3, 20% by weight aqueous solution of chondroitin was added, respectively, in the amount of 20% by weight with respect to the filler. The fillers were tested as in Example 1, and good results as Example 1 were obtained.

EXAMPLE 6

To the bone filler of Examples 1, 2 and 3, 20% by weight aqueous solution of collagen was added, respectively, in the amount of 20% by weight with respect to the filler. The fillers were tested as in Example 1, and good results as Example 1 were obtained.

We claim:

1. A method of filling a void in a bond which comprises filling the void with a fibrous bone filler comprising fibers containing intact hydroxyl apatite formed by solution spinning an aqueous suspension comprised of 5 to 70 percent by weight of hydroxyl apatite, 5 to 40 percent by weight of a water-soluble binder and 10 to 90 percent by weight of water, wherein said fibrous bone filler is immersed in an immersion liquid selected from the group consisting of water, physiological saline, chondroitin solution, and hyaluronic solution.

2. The method of claim 1, wherein the content of the intact hydroxyl apatite in the fiber is at least 25%.

3. The method of claim 2, wherein the content of the intact hydroxyl apatite in the fiber is at least 50%.

4. The method of claim 3, wherein the fiber essentially consists of intact hydroxyl apatite.

5. The method of claim 1, wherein the bone filler is in the form of a non-woven fabric, cotton, absorbent cotton, or roving.

6. The method of claim 1, wherein the fiber contains a reinforcing material.

7. The method of claim 6, wherein the reinforcing material is $Ca_3PO_4$.

8. The method of claim 1, wherein the diameter of the fiber is about 1 to 30 μm.

9. The method of claim 8, wherein the diameter of the fiber is about 1 to 30 μm.

10. The method of claim 1, wherein said immersion liquid is in an amount of from 1 to 20% by weight of said fibrous bone filler.

11. The method of claim 1, wherein said immersion liquid is in an amount of from 5 to 10% by weight of said fibrous bone filler.

12. The method of claim 1, wherein said immersion liquid is selected from the group consisting of chondroitin solution and hyaluronic solution, and wherein said immersion liquid is a solution with water as a solvent and with a solute concentration of about from 1 to 20% by weight of said immersion liquid.

13. The method of claim 11, wherein said immersion liquid is selected from the group consisting of chondroitin solution and hyaluronic solution, and wherein said immersion liquid is a solution with water as a solvent and with a solute concentration of about from 1 to 20% by weight of said immersion liquid.

14. The method of claim 4, wherein said immersion liquid is in an amount of from 1 to 20% by weight of said fibrous bone filler.

15. The method of claim 7, wherein said immersion liquid is in an amount of from 1 to 20% by weight of said fibrous bone filler.

16. The method of claim 9, wherein said immersion liquid is in an amount of from 1 to 20% by weight of said fibrous bone filler.

17. The method of claim 1, wherein said water-soluble binder is selected from the group consisting of polyvinyl alcohol, carboxymethyl cellulose, hydroxylpropyl cellulose, collagen, pullulan and chitin.

18. The method of claim 17, wherein said water-soluble binder is pullulan.

19. The method of claim 1, wherein said aqueous suspension is comprised of 15 to 20 percent by weight of hydroxyl apatite, 20 to 25 percent by weight of a water-soluble binder and 60 to 65 percent by weight of water.

20. The method of claim 1, wherein said aqueous suspension is comprised of 15 to 30 percent by weight of hydroxyl apatite, 15 to 30 percent by weight of a water-soluble binder and 50 to 70 percent by weight of water.

* * * * *